United States Patent [19]

Tiab et al.

[11] Patent Number: 5,193,059
[45] Date of Patent: Mar. 9, 1993

[54] METHOD FOR IDENTIFYING AND CHARACTERIZING HYDRAULIC UNITS OF SATURATED POROUS MEDIA: TRI-KAPPA ZONING PROCESS

[75] Inventors: Djebbar Tiab, Norman, Okla.; David M. Marschall, Sugar Land; Mehmet H. Altunbay, Houston, both of Tex.

[73] Assignee: Western Atlas International Inc., Houston, Tex.

[21] Appl. No.: 784,641

[22] Filed: Oct. 28, 1991

Related U.S. Application Data

[63] Continuation of Ser. No. 534,458, Jun. 6, 1990, abandoned.

[51] Int. Cl.$^5$ .............................................. G01V 1/00
[52] U.S. Cl. .................................................... 364/422
[58] Field of Search ................... 364/422; 73/152, 155

[56] References Cited

U.S. PATENT DOCUMENTS

| | | | |
|---|---|---|---|
| 4,742,459 | 5/1988 | Lasseter | 364/422 |
| 4,752,882 | 6/1988 | Givens | 364/422 |
| 4,764,903 | 8/1988 | Siebert | 364/422 |
| 4,773,264 | 9/1988 | Herron | 364/422 |
| 4,779,200 | 10/1988 | Bradbury et al. | 364/422 |
| 4,868,751 | 9/1989 | Dogru et al. | 364/422 |
| 4,890,487 | 1/1990 | Dussan et al. | 364/422 |
| 4,903,207 | 2/1990 | Alger et al. | 364/422 |
| 4,903,527 | 2/1990 | Herron | 364/422 |

OTHER PUBLICATIONS

J. Kozeny, "Uber Die Kapillare Leitung des Wassers im Boden," 136a *Sitz. Ber. Akademia, Wiss. Wien., Math. Nat.* (Abt. 11 a) 271 (1927).

P. C. Carman, "Fluid Flow Through Granular Beds," 15 *Trans. Inst. Chem. Engs.* 150 (1937).

B. B. Mandelbrot, *The Fractal Geometry of Nature*, W. H. Freeman and Co. (1983).

C. S. Brooks & W. R. Purcell, "Surface Area Measurements on Sedimentary Rocks," 195 *Petroleum Transactions, AIME* 289 (1952).

E. M. Tignor, J. F. Noonan, & W. N. Lockwood, "Pore Studies of Petroleum-Reservoir Sandstones," *Producers Monthly* May 16, 1952).

F. M. Nelson & F. T. Eggertsen, "Determination of Surface Area Adsorp ion Measurements by a Continuous Flow Method," 30 *Analytical Chemistry* 1387 (Aug. 1957).

E. C. Donaldson, R. F. Kendall, B. A. Baker, & F. S. Manning, "Surface-Area Measurement of Geologic Materials," *Society of Petroleum Engineers Journal* 111 (Apr. 1975).

R. T. Johansen, P. B. Lorenz, C. G. Dodd, Pidgeon, D. Frances, & J. W. Davis, "The Permeation of Water and Isooctane Through Plugs of Microscopic Particles of Crushed Quartz," 57 *Journal of Physical Chemistry* 40 (1953).

H. Pape, L. Riepe, & J. R. Schopper, "A Pigeon-Hole Model for Relating Permeability to Specific Surface," *The Log Analyst* 5 (Jan.-Feb. 1982).

G. E. Archie, "The Electrical Resistivity Log as an Aid in Determining Reservoir Characteristics," 146 *Transactions, AIME* 54 (1942).

M. P. Tixier, "Electric-Log Analysis in the Rocky Mountains," 48 *Oil and Gas Journal* 143 (1949).

(List continued on next page.)

Primary Examiner—Roy N. Envall, Jr.
Assistant Examiner—X. Chung
Attorney, Agent, or Firm—E. Eugene Thigpen

[57] ABSTRACT

The present invention is a method of logging a formation for permeability using a logging tool that is calibrated to dynamically correlate macroscopic porosity measurements to microscopic permeability measurements for the formation. The correlation is determined from hydraulic unit characterization factors which are calculated from parameters of the formation determined in an analysis of core material taken from the hydraulic units determined to be in the geologic units. The hydraulic units are identified from the relationship of direct permeability and porosity measurements with calculated hydraulic unit characterization factors for the formation.

13 Claims, 7 Drawing Sheets

OTHER PUBLICATIONS

M. C. Leverett, "Capillary Behavior in Porous Solids," *Petroleum Technology* 152 (Aug. 1940).

W. D. Rose & W. A. Bruce, "Evaluation of Capillary Character in Petroleum Reservoir Rock," 186 *Petroleum Transactions, AIME* 127 (1949).

R. J. Wyllie & W. D. Rose, "Some Theoretical Considerations Related to the Quantitative Evaluation of the Physical Characteristics of Reservoir Rock from Electrical Log Data," 189 *Petroleum Transactions, AIME* 105 (1950).

P. M. Adler, "Fractal Porous Media III: Transversal Stokes Flow Through Random and Sierpinski Carpets," *Transport in Porous Media* 3 185 (1988).

G. E. Archie, "Electrical Resistivity as Aid in Core-Analysis Interpretation," 31 *Bulletin AAPG* 350 (1947).

J. H. Thomeer, "Air Permeability as a Function of Three Pore-Network Parameters," *Journal of Petroleum Technology* 809 (Apr. 1983).

J. H. Thomeer, "Introduction of a Pore Geometrical Factor Defined by the Capillary Pressure Curve," *Journal of Petroleum Technology* 73 (Mar. 1960).

K. Ruzyla, "Limitations and Pitfalls of Using Quantitative Image Analysis for Reservoir Assessment," 72 AAPG Bulletin 243 (1988).

J. D. Wells & J. O. Amaefule, "Capillary Pressure and Permeability Relationships in Tight Gas Sands," *SPE/DOE No. 13879* (May 1985).

J. O. Amaefule, D. G. Kersey, D. M. Marschall, J. D. Powell, L. E. Valencia, D. K. Keelan, "Reservoir Description: A Practical Synergistic Engineering and Geological Approach Based on Analysis of Core Data," *SPE No. 18167* (1988).

D. K. Keelan, "Core Analysis for Aid in Reservoir Description," *Journal of Petroleum Technology* 2483 (Nov. 1982).

N. C. Wardlaw, "Pore Geometry of Carbonate Rocks as Revealed by Pore Casts and Capillary Pressure," 60 *AAPG Bulletin* 245 (1976).

R. Ehrlich & B. Weinberg, "An Exact Method for Characterization of Grain Shape," 40 *Journal of Sedimentary Petrology* 205 (1970).

D. G. Jorgenson, "Estimating Permeability in Water-Saturated Formations," *The Log Analylist* 401 (Nov.-Dec. 1988).

F. J. Lucia, "Petrophysical Parameters Estimated From Visual Descriptions of Carbonate Rocks: A Field Classification of Carbonate Pore Space," *Journal of Petroleum Technology* 629 (Mar. 1983).

W. Rose, "A Rational Scheme for Calculating Sidewall Core Permeability," *The Log Analyst* 21 (Mar.-Apr. 1986).

C. Perez-Rosales, "Stimulaneous Determination of Basic Geometrical Characteristics of Porous Media," *SPE Journal* 413 (Dec. 1969).

M. M. Herron, "Estimating the Intrinsic Permeability of Clastic Sediments from Geochemical Data," SPWLA Twenty-Eighth Annual Logging Symposium (Jun. 1987).

L. L. Raymer, "Elevation and Hydrocarbon Density Correction for Log-Derived Permeability Relationships," *The Log Analyst* 3 (May-Jun. 1981).

K. Ruzyla, "Characterization of Pore Space by Quantitative Image Analysis," *SPE Formation Evaluation* 389 (Aug. 1986).

Z. Barlai, N. A. Berruin, & R. Abdel Mawla, "Determination of Capillary Displacement Pressure & Representative Average Capillary Pressure Versus Depth in Shaley Sandstones From Well Logs," *SPWLA Twenty-Second Annual Logging Symposium* (Jun. 1981).

METHOD FOR IDENTIFYING AND CHARACTERIZING HYDRAULIC UNITS OF SATURATED POROUS MEDIA: TRI-KAPPA ZONING PROCESS

This is a continuation of copending application Ser. No. 07/534,458 filed on Jun. 6, 1990, now abandoned.

BACKGROUND OF THE INVENTION

The present invention relates to methods for modeling the quality and performance of a reservoir that contains hydrocarbon fluids, and more particularly, to methods for predicting the flow characteristics of a reservoir of hydrocarbon fluids. Still more particularly, the present invention relates to a method for identifying and characterizing units of a formation having similar hydraulic characteristics based on microscopic measurements of rock core samples and for linking the hydraulic units to wireline logs to enable accurate prediction of formation flow characteristics therefrom.

Traditional techniques for making macroscopic measurements of reservoir characteristics, like wireline logs, are unable to measure reservoir dynamic functions, such as formation permeability. Instead, reservoir engineers must rely on microscopic measurements of permeability derived from data obtained on core samples and on empirical or regressional correlations between permeability and log-derived porosity measurements to predict formation permeability. Permeability measurements derived from core samples are accurate and give precise inch by inch or foot by foot descriptions of formation permeability, but are difficult to scale to reservoir size. Quantitative correlations between porosity and permeability are not satisfactory due to the absence of a suitable transform for predicting permeability based on porosity.

Industry has relied on the Kozeny equation and empirical studies to establish relationships between macroscopic formation measurements and formation fluid flow characteristics. Kozeny reported that a number of variables not previously considered, including specific surface areas of the pore system, tortuosity, and shape of the pore system, affected the relationship between porosity and permeability. See J. Kozeny, "Uber Die Kapillare Leitung des Wassers im Boden," 136a *Sitz. Ber., Akademie Wiss. Wien., Math. Nat. (Abt. IIa)* 271 (1927). Using a simple model of a bundle of capillary tubes, Kozeny derived an expression for the relationship between porosity and permeability, as follows:

$$k = \frac{\phi}{2S_{pv}^2} \quad (1)$$

where k is permeability (cm$^2$), $\phi$ is porosity (no units), $S_{pv}$ is the internal surface area of the pore space per unit of pore volume, and 2 is a constant (the "Kozeny constant"). For unconsolidated formations, Equation 1 becomes:

$$k = \frac{1}{2S_{gv}^2} \frac{\phi^3}{(1-\phi)^2} \quad (2)$$

where $S_{gv}$ is the specific surface area of a porous material per unit of grain volume. Kozeny's model has gained general acceptance in the industry as a descriptor of the porosity-permeability relationship.

Carman recognized that textural parameters, such as size, sorting, shape, and spatial distribution of grains have a substantial impact on formation permeability. See P. C. Carman, "Fluid Flow Through Granular Beds," 15 *Trans. Inst. Chem. Engs.* 150 (1937). Carman adapted the Kozeny equation for formations comprised of uniform and homogeneous rocks having a dominance of nearly spherical grains by changing the Kozeny constant from 2 to 5. Carman's adaptation is also a widely used form of the Kozeny equation.

Neither the Kozeny nor the Kozeny-Carman models accurately characterize the relationship between porosity and permeability because reservoir formations never conform to the assumed capillary tube or spherical grain models. The lack of general applicability of the Kozeny and Kozeny-Carman equations led researchers to search for formation-specific empirical correlations between porosity and permeability. Such empirical correlations have been poor, however, and in the absence of plausible physical models to explain the predicted relationships, they have not gained wide acceptance.

A number of researchers have investigated the relationship between well log data and permeability. See M. R. Wyllie & W. D. Rose, "Some Theoretical Considerations Related to the Quantitative Evaluation of the Physical Characteristics of Reservoir Rock from Electrical Log Data," 189 *Petroleum Transactions, AIME* 105 (1950); W. D. Rose & W. A. Bruce, "Evaluation of Capillary Character in Petroleum Reservoir Rock," 186 *Petroleum Transactions, AIME* 127 (1949); M. P. Tixier, "Electric Log Analysis in the Rocky Mountains," 48 *Oil and Gas Journal* 143 (1949); G. E. Archie, "The Electrical Resistivity Log as an Aid in Determining Reservoir Characteristics," 146 *Petroleum Transactions, AIME* 54 (1942); M. C. Leverett, "Flow of Oil-Water Mixtures Through Unconsolidated Sands," 132 *Petroleum Transactions, AIME* 149 (1939). These researchers pioneered different correlations relating cementation factor, resistivity index, saturation, permeability, and porosity. Wyllie and Rose also pointed out that these parameters are closely related to the textural parameters of formation rocks expressed in the Kozeny equation and to expressions of capillary pressure phenomena. None of these researchers, however, was able to construct an accurate correlation between porosity and permeability. Each concluded that accurate estimates of reservoir rock parameters should not be made from log data alone, but from a combination of core analysis and log data.

Amaefule, et al. observe that the "mean hydraulic radius" ($(k/\phi)^{\frac{1}{2}}$), calculated from permeability and porosity data derived from core sample analysis, relates Darcy flow properties to pore space attributes. See J. O. Amaefule, D. G. Kersey, D. M. Marschall, J. D. Powell, L. E. Valencia, D. K. Keelan, "Reservoir Description: A Practical Synergistic Engineering and Geological Approach Based on Analysis of Core Data," *SPE No.* 18167 (1988). Amaefule, et al. note that core analysis descriptions can be used to divide the reservoir into various hydraulic units. They use the concept of a mean hydraulic radius to develop relationships between microscopic pore level attributes and macroscopic core data to establish zones with similar hydraulic quality. Amaefule, et al. discuss conceptually the desireability of establishing relationships between core data and well log data, such as porosity, but no such relationships are developed in their paper.

The Kozeny and Kozeny-Carman constants, 2 and 5, are valid only for the capillary tube and spherical grain models, respectively. These models, as previously noted, do not translate accurately to the general case in which the porous media do not conform to the models. In the general case, permeability varies with a variety of characteristics other than porosity, including pore shape and size, grain shape and size, pore and grain distribution, tortuosity, cementation, and type of pore system, that is, intergranular, intercrystalline, vuggy, or fractured. These characteristics vary from one lithology to another and even within formation units of similar lithology. Thus, they cannot be modelled accurately as a constant.

It would be desirable to provide a method for determining the permeability of a formation based on macroscopic data available from a well log. Such a method preferably would take account of variances in permeability as a consequence of pore shape and size, grain shape and size, pore and grain distribution, tortuosity, cementation, and type of pore system.

SUMMARY OF THE INVENTION

Accordingly, there is provided herein a method for defining formation units of similar hydraulic characteristics by means of core measurements and for relating the hydraulic characteristics of such units to macroscopic measurements of the formation as provided by wireline logs. The method includes the steps of (a) obtaining core samples of the formation material from which a complete lithologic description of the formation may be made, (b) measuring directly the permeability, k, and the porosity, $\phi$, of discrete samples of material taken from the recovered core, (c) determining a hydraulic unit characterization factor, $H_c$, as the product of an effective zoning factor, $K_T$, and the square of the specific surface area of the pore system or the formation grains; (d) plotting log ($H_c$) versus log ($\phi$) and log (k) versus log ($H_c$); and (e) logging for permeability by obtaining a wireline log of porosity and converting the porosity measurements to permeability measurements by means of the relationship established in step (d).

The method of the present invention provides an accurate transformation from pore space attributes to macroscopic scale properties of a reservoir by integrating core analysis data with wireline log data. This transformation eliminates empirical and subjective calibration algorithms for wireline logging tools by providing measured and calculated characteristics for the formation in question. The correlation between $H_c$ and both permeability and porosity is based on recognition that certain textural parameters that affect both permeability and porosity vary within the fomation and cannot be modelled accurately by means of the Kozeny or Kozeny-Carman constants. These variable textural parameters are accounted for in the present inventive method by means of the effective zoning factor, $K_T$, of which the hydraulic unit characterization factor is a product.

These and various other objects and advantages of the present invention will become readily apparent to those skilled in the art upon reading the following detailed description and claims and by referring to the accompanying drawings.

BRIEF DESCRIPTION OF THE DRAWINGS

For a detailed description of the preferred embodiment of the invention, reference will be made now to the accompanying drawings, wherein.

DESCRIPTION OF THE PREFERRED EMBODIMENT

Reservoirs containing hydrocarbon fluids are commonly evaluated based on the volume of recoverable fluids trapped within the reservoir and the rate at which the fluids can be produced. Formation "permeability" measure of the ability of a formation to allow the flow of fluids through its interconnected pore spaces. Permeability, however, cannot be measured foot by foot throughout a formation by conventional wireline logging techniques. Instead, permeability is calculated for available core samples at discrete point depths by making necessary core measurements and applying Darcy's law.

Researchers have long sought to establish a correlation between parameters measured on a macroscopic scale, such as formation porosity measured by a wireline log, and permeability measured in a laboratory. These efforts include the Kozeny and Kozeny-Carman models, as well as formation-specific correlations between porosity and permeability. Neither approach has translated successfully to the general case. The Kozeny and Kozeny-Carman models are limited substantially by the geometric configurations assumed by the models. Formation specific correlations are generally poor, because permeability, although related to porosity, is affected by many additional parameters that complicate the relationship. These complicating parameters, as approximated by Kozeny and Carman, are not measurable on a macroscopic scale.

In accordance with the principles of the present invention, the Kozeny model is modified to account for the variable effect of formation textural parameters that affect permeability. As described in greater detail below, the relationship between porosity and permeability in the general case varies with an effective zoning factor, $K_T$, which is a function of pore shape and size, grain shape and size, pore and grain distribution, tortuosity, cementation, and type of pore system. Using direct measurements of a hydraulic unit characterization factor, $H_c$, itself a function of $K_T$, and plots of $H_c$ versus porosity and of permeability versus $H_c$, one can establish a relationship, valid in the general case, between microscopic measurements of formation parameters, such as permeability, and macroscopic measurements of parameters such as porosity. Using $H_c$ as the transformation for each hydraulic unit, one can calibrate a wireline logging tool to measure formation permeability and its variances throughout a formation and thereby have a complete and accurate assessment of formation flow characteristics based on a wireline log of a well.

Figure 1:
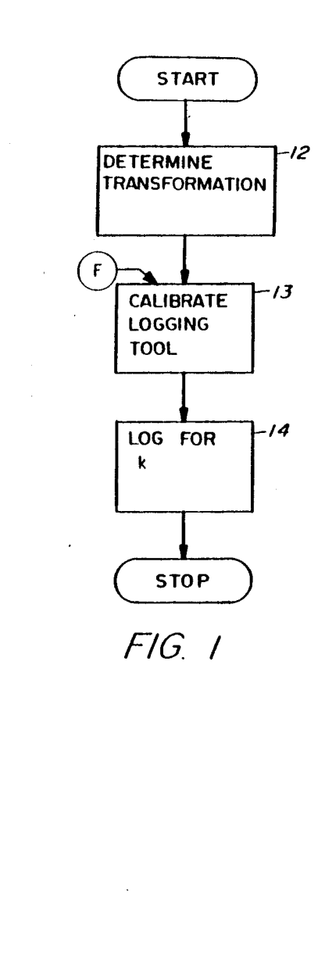
FIG. 1 is a flow diagram of a method for logging a well for permeability.

More particularly, the present invention comprises a method for measuring formation permeability based on macroscopic wireline log measurements of formation characteristics. As shown in FIG. 1, the inventive method comprises three basic steps. The first step 12 is determining a transformation from microscopic core measurements to macroscopic wireline log measurements. The second step 13 is calibrating the wireline logging tool, based on the transform determined in step 12, to measure permeability as a function of macroscopic parameters such as porosity. The third step 14 is logging a well for formation permeability.

Figures 2, 3:
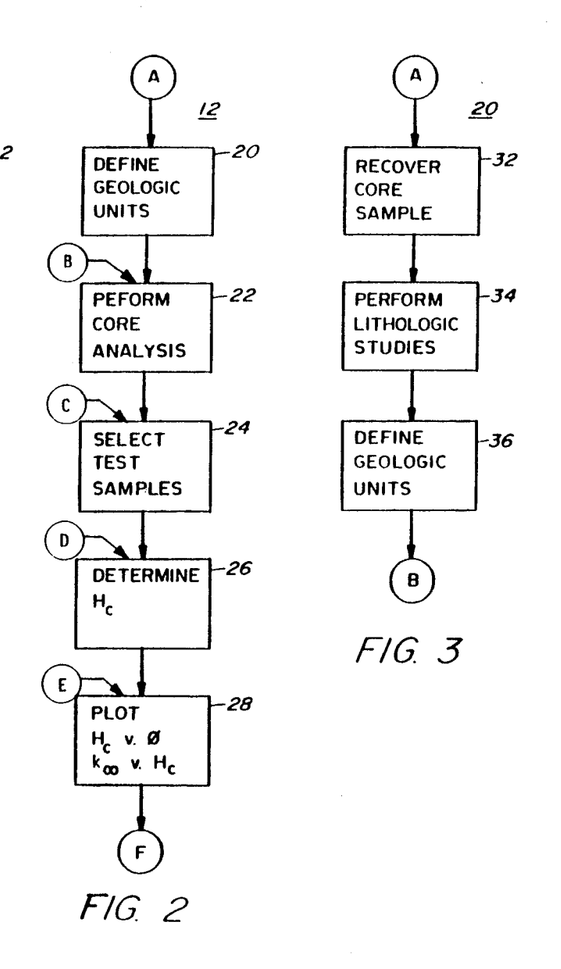
FIG. 2 is a flow diagram of the method for determining a transform from microscopic core measurements to macroscopic wireline log measurements.
FIG. 3 is a flow diagram for step 20 of the method described in FIG. 2.

FIG. 2 describes in general terms the first step 12 of FIG. 1, the method for determining a transformation from microscopic core measurements to macroscopic wireline log measurements. The first step 20 involved in determining the transformation is defining geologic/lithologic units of formation material based on a core sample. The second step 22 is performing a complete core analysis on the core sample, measuring in particular the Klinkenberg permeability and the porosity of formation samples, preferably at overburden pressure conditions. The next step 24 is selecting formation samples for further testing based on calculated values for a hydraulic unit characterization factor, $H_c$. The fourth step 26 is determining the hydraulic unit characterization factor, $H_c$, based on microscopic measurements on the selected samples. The final step 28 is plotting $H_c$ versus permeability and plotting porosity versus $H_c$ to establish a link between macroscopic porosity measurements and formation permeability for the corresponding hydraulic units of formation.

FIG. 3 shows the steps comprising the step 20 of defining geologic units. As shown in FIG. 3, the step of defining geologic units comprises the steps of recovering a diamond-cut core sample using conventional techniques (step 32), making a complete lithologic description of the recovered core, again using conventional methodology (step 34), and based on the lithologic description, defining the geologic units comprising the formation (step 36).

Geologic units are areas within the formation having similar lithologic characteristics. Geologic units most often, but need not, correspond to hydraulic units, that is, areas within the formation having similar flow characteristics. Geologic units may encompass one or more hydraulic units. The goal of the calibration portion of the method disclosed herein is to define discrete hydraulic units within the formation and to relate macroscopic parameters measured within those hydraulic units to microscopic parameters like permeability. The first step in identifying the hydraulic units is to define the geologic units, as described in steps 32, 34, and 36.

Figure 4:
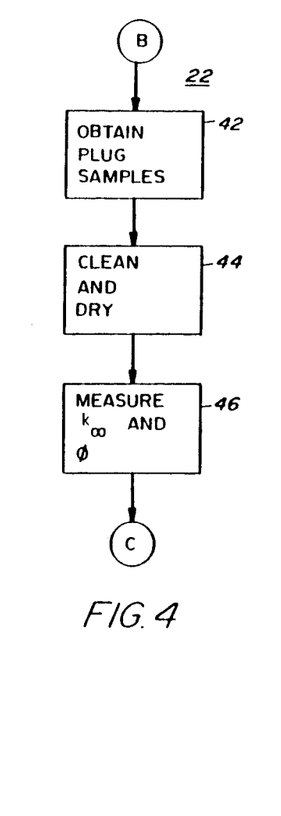
FIG. 4 is a flow diagram for step 22 of the method described in FIG. 2.

FIG. 4 describes in greater detail the three steps comprising the step 22 of performing core analysis of the recovered core sample. These include obtaining a series of plug samples from the core recovered in step 32 (step 42), cleaning and drying the sample material (step 44), and making direct measurements of permeability and porosity, preferably at overburden pressure conditions, on the material from the plug samples (step 46). Direct measurements of permeability and porosity are essential to the process of establishing the relationship between permeability, porosity, specific surface area of pore or grain volume, and the effective zoning factor, $K_T$. These relationships, in turn, enable construction of the relationship between macroscopic porosity and microscopic permeability.

The permeability and porosity measurements can be made by conventional plug sample analysis techniques, preferably at overburden pressure conditions or at a pressure of at least 800 lbs. or more. Overburden pressure conditions are necessary to represent rock properties at in situ conditions. This is particularly critical for highly stress sensitive formations, such as unconsolidated or friable formations, or tight formations where small stresses begin restricting pore throats.

For permeability, it is preferable to measure the equivalent liquid nonreactive permeability, also known as the Klinkenberg permeability, $k_\infty$, rather than the air permeability. Unlike air permeability measurements, the Klinkenberg permeability measurement is not sensitive to fluctuations in mean pressure. Air permeability measurements, particularly in low permeability rock, introduce substantial amounts of uncertainty into the calculations, making air permeability measurements less desirable.

Figure 5:
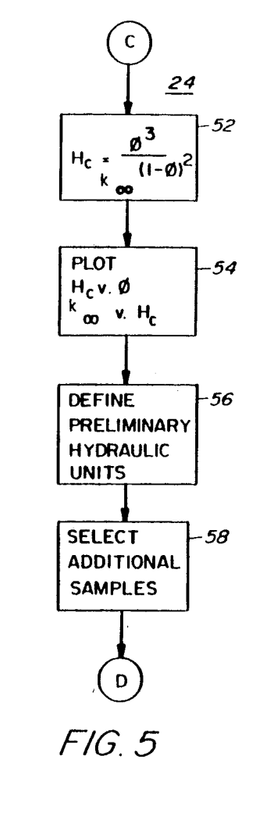
FIG. 5 is a flow diagram for step 24 of the method described in FIG. 2.

FIG. 5 summarizes the steps comprising the third step (step 24 in FIG. 2) of the process of determining the transformation from microscopic to macroscopic data. The first such step (step 52) comprises calculating the hydraulic unit characterization factor, $H_c$, for each of the plurality of plug samples, based on the measurements of Klinkenberg permeability, $k_\infty$, and porosity, $\phi$, as follows:

$$H_c = \frac{\phi^3}{k_\infty(1-\phi)^2} \qquad (3)$$

The other three steps include plotting $H_c$ versus $\phi$ and $k_\infty$ versus $H_c$ for each discrete geologic unit as previously identified (step 54), identifying preliminarily the hydraulic units comprising each geologic unit (step 56), and selecting samples of the core material for subsequent testing based on the preliminary definition of hydraulic units (step 58).

As will become evident after reading the discussion set forth below regarding the remaining steps in the process of determining the transformation, the logarithm of the hydraulic unit characterization factor varies directly with the logarithm of porosity and with the logarithm of permeability. Log-log plots of $H_c$ versus $\phi$ and k versus $H_c$ for each geologic unit typically reveal one or more sloping lines, each of which corresponds to a different hydraulic unit within the geologic unit under scrutiny. Log-log plots of the calculated $H_c$ and the measured $k_\infty$ and $\phi$ will yield an approximation for the distribution of hydraulic units within each geologic unit. Based on these approximate distributions of hydraulic units, one can target certain areas of the formation as contained in the recovered core sample for additional examination, as described below.

The next step (26 in FIG. 2) in the process of determining the transformation is to determine a measured value for the hydraulic unit characterization factor, $H_c$, from analysis of each of a plurality of samples selected from the core sample. By definition, the hydraulic unit characterization factor, $H_{cp}$, for consolidated (pore) formations is:

$$H_{cp} = K_T S_{pv}^2 \qquad (4)$$

where $S_{pv}$ is the internal surface area of pore space per unit of pore volume. For unconsolidated (grain) formations, the hydraulic unit characterization factor ($H_{cg}$) is defined as:

$$H_{cg} = K_T S_{gv}^2 \qquad (5)$$

where $S_{gv}$ is the specific surface area of grain per unit of grain volume. The effective zoning factor, $K_T$, as previously noted, is a function of the various formation textural parameters that affect permeability.

Figure 6:
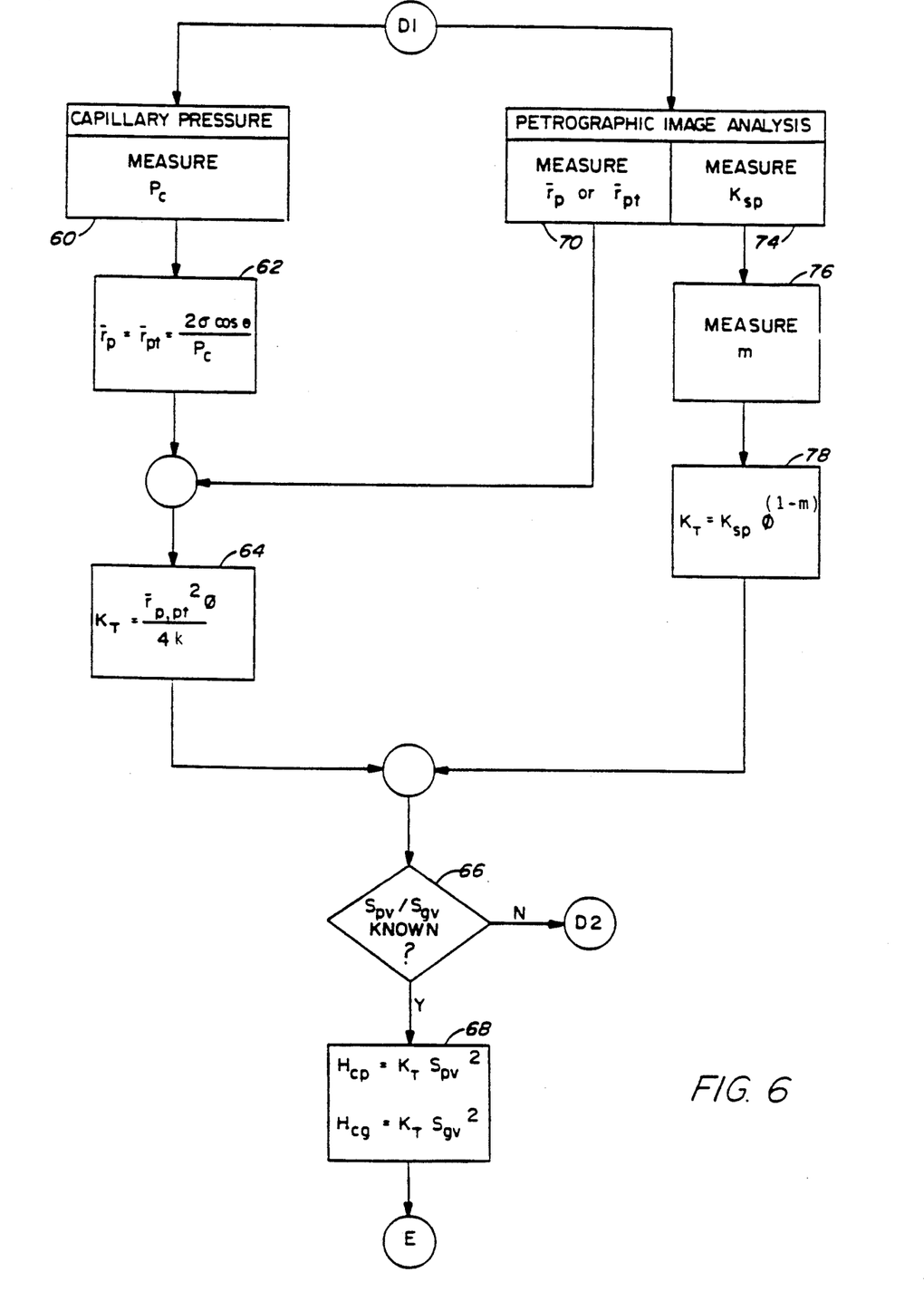
FIG. 6 is a flow diagram for a portion of step 26 of the method described in FIG. 2.
Figure 7:
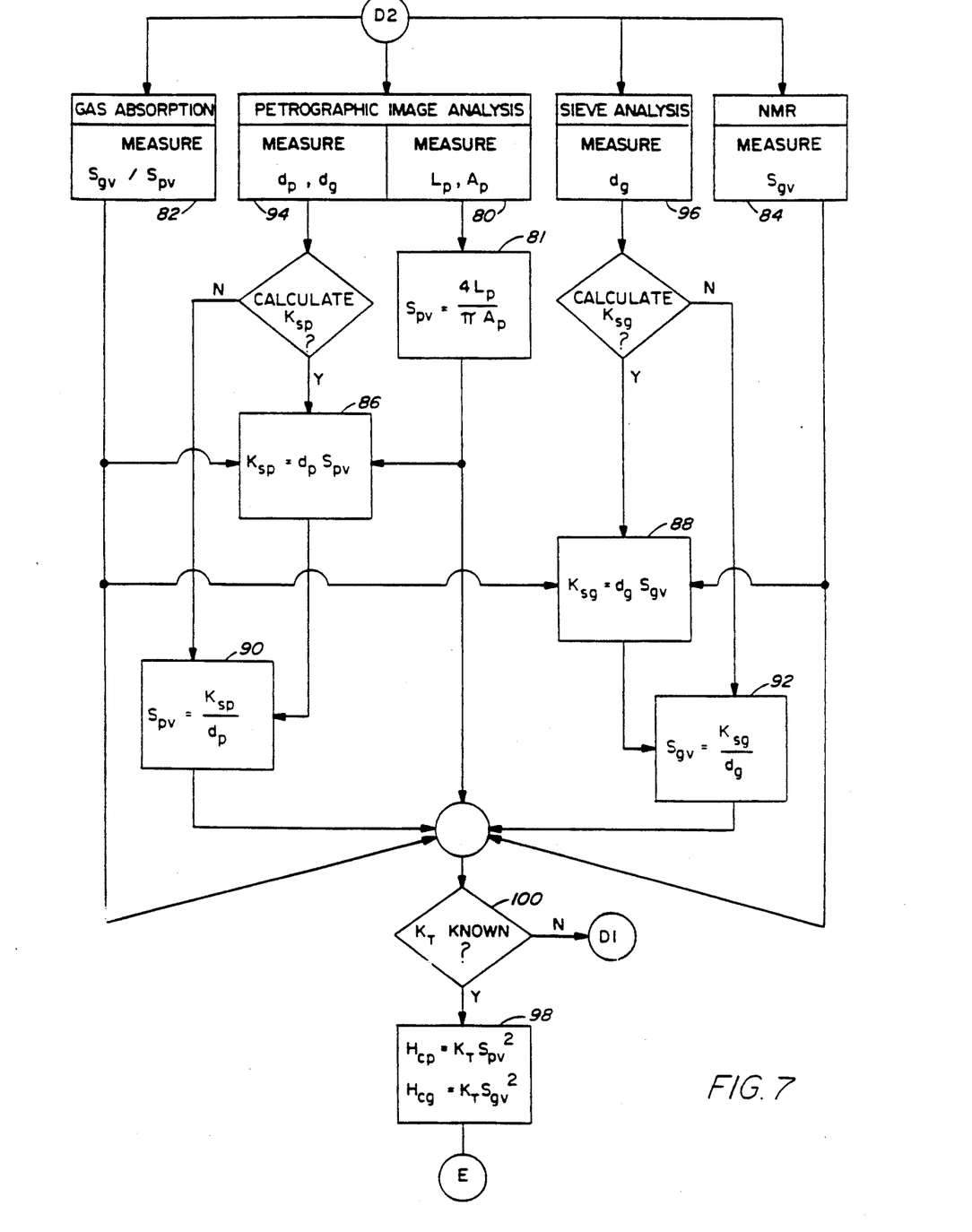
FIG. 7 is a flow diagram for a portion of step 26 of the method described in FIG. 2.

In order to obtain a measured value for $H_c$, one must determine $K_T$ by measuring either $S_{gv}$ or $S_{pv}$ and either $d_g$ (grain diameter) or $d_p$ (pore diameter), respectively, for each selected sample. Given the variety of core analysis techniques currently available, there is no unique approach to measuring $H_c$. The preferred approach will vary according to the type of formation involved, that is, consolidated or unconsolidated, and the tools available for analysis of core samples. It is desirable to determine $H_c$ by two independent methods in order to compare and verify the results. FIGS. 6 and 7 describe some of the preferred techniques for measuring $K_T$ and $S_{gv}$ or $S_{pv}$, respectively.

Referring now to FIG. 6, capillary pressure measurements by conventional techniques (step 60) allow determination of the the mean pore throat radius, $\bar{r}_{pt}$, depending on whether imbibition or drainage is employed, (step 62) as follows:

$$\bar{r}_p \text{ or } \bar{r}_{pt} = \frac{2\sigma \cos(\theta)}{P_c} \qquad (6)$$

where $P_c$ is the capillary pressure (lbs/in$^2$), $\sigma$ is the interfacial tension (dyne/cm), and $\theta$ is the contact angle. Using measurements of k and $\phi$ on the same sample, one can calculate the effective zoning factor, $K_T$, (step 64) as follows:

$$K_T = \frac{\bar{r}_p^2 \phi}{4k} \text{ or } K_T = \frac{\bar{r}_p^2 \phi}{4k} \qquad (7)$$

If a surface area measurement, $S_{pv}$ or $S_{gv}$, is then available on the same sample, one can calculate the hydraulic unit characterization factor, $H_c$, at that point (step 68) by means of Equation (4) or Equation (5), above. If no surface area measurement is then available, one must obtain the surface area data by means such as are disclosed herein with reference to FIG. 7 (step 66).

Referring still to FIG. 6, petrographic image analysis offers at least two approaches to determining the effective zoning factor, $K_T$. First, one can measure directly the mean pore radius, $\bar{r}_p$, or the mean pore throat radius, $\bar{r}_{pt}$ (step 70). One can then determine the effective zoning factor, $K_T$, from Equation (7), above, (step 64) and proceed to determine $H_c$ as explained for capillary pressure measurements (steps 66 and 68).

Alternatively, one can measure the pore shape factor, $K_{sp}$, using petrographic image analysis (step 74). The effective zoning factor, $K_T$, can then be determined by measuring the cementation factor, m, using conventional core analysis techniques (step 76), and calculating $K_T$ as a function of tortuosity, $\tau$, (step 78) as follows:

$$\tau = \phi^{1-m} \qquad (8)$$

$$K_T = \tau K_{sp} \qquad (9)$$

The hydraulic unit characterization factor, $H_c$, can then be determined as explained above in connection with steps 66 and 68.

FIG. 7 describes several of the various alternatives for determining the surface area measurements needed to determine $H_c$. Several measurement techniques can be used to measure surface area directly. The surface area of pore volume, $S_{pv}$, can be determined by use of petrographic image analysis (step 80) by measuring pore perimeter, $L_p$, and pore cross-sectional area, $A_p$, and then calculating the effective pore shape factor (step 81) as follows:

$$S_{pv} = \frac{4L_p}{\pi A_p} \qquad (10)$$

The pore shape factor, $K_{sp}$, can also be determined by use of Brunauer Emmet Teller ("BET") gas absorption analysis (step 82), although BET analysis is not preferred for use in measuring pore surface area. This follows from the fact that most consolidated formations encompass a substantial volume of "dead-end" pores that have little or no impact on fluid flow within the formation. These dead-end pores are nonetheless detected and measured in gas absorption analysis, giving rise to an error in the determination of $H_c$.

Referring still to FIG. 7, the surface area of grain per unit volume of grain, $S_{gv}$, can be measured directly by means of BET gas absorption analysis (step 82) or by means of nuclear magnetic resonance (step 84). Alternatively, because the pore shape factor, $K_{sp}$, is formation specific, the specific surface areas may be determined by calculating $K_{sp}$ and $K_{sg}$ for a given hydraulic unit (steps 86 and 88), as follows:

$$K_{sp} = d_p S_{pv} \qquad (11)$$

$$K_{sg} = d_g S_{gv} \qquad (12)$$

where $d_p$ and $d_g$ are the pore and grain diameters, respectively, and $S_{pv}$ and $S_{gv}$ are determined as described above. The specific surface areas for other samples in the same hydraulic unit then can be calculated (steps 90 and 92) from measurements of the pore and grain diameters, as follows:

$$S_{pv} = \frac{K_{sp}}{d_p} \qquad (13)$$

$$S_{gv} = \frac{K_{sg}}{d_g} \qquad (14)$$

Pore diameter, $d_p$, can be determined by petrographic image analysis (step 94), and grain diameter, $d_g$, can be determined by sieve analysis.

Grain diameter, $d_g$, data is useful for depositional model studies where fining upward or coarsening upward sequences are noted on well logs. A transformation from wireline-measured porosity to grain diameter, allowing one to log for grain diameter, may be accomplished by applying the method described herein and the following approximation:

$$d_g = \frac{2K_{sg}}{K_{sp}}\left(\frac{1}{\phi} - 1\right)\bar{r}_p, \quad (15)$$

where $\bar{r}_p$ is determined by capillary pressure measurements.

Once at least one of the specific surface areas, $S_{pv}$ or $S_{gv}$, is known, assuming that the effective zoning factor, $K_T$, is known, the hydraulic unit characterization factor, $H_c$, can be determined by use of equation (4) or equation (5) (step 98). If $K_T$ for the sample in question is not known, then the techniques described above in connection with FIG. 6 should be employed to make that determination (step 100).

Figure 8:
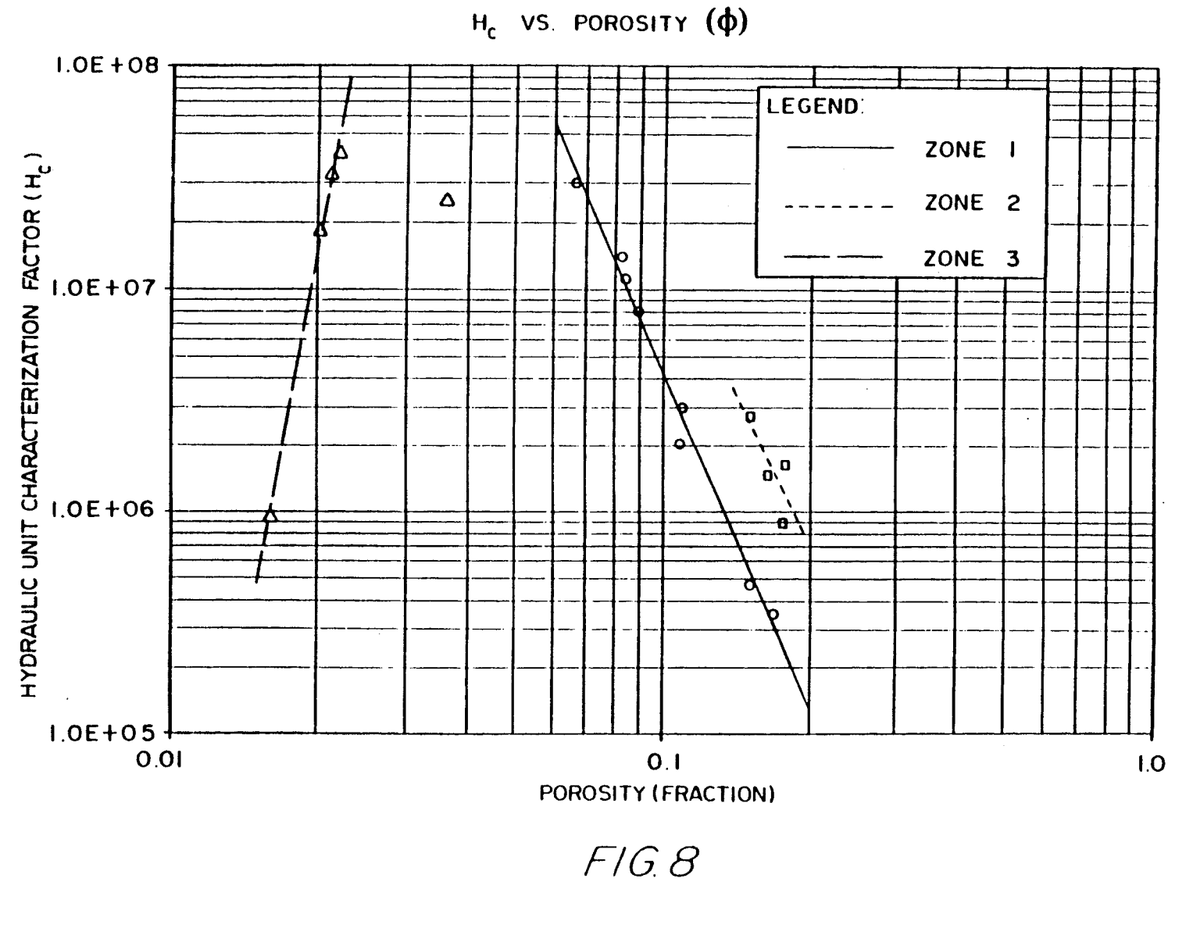
FIG. 8 is a graph showing an example of a plot of log ($H_c$) versus log ($\phi$)
Figure 9:
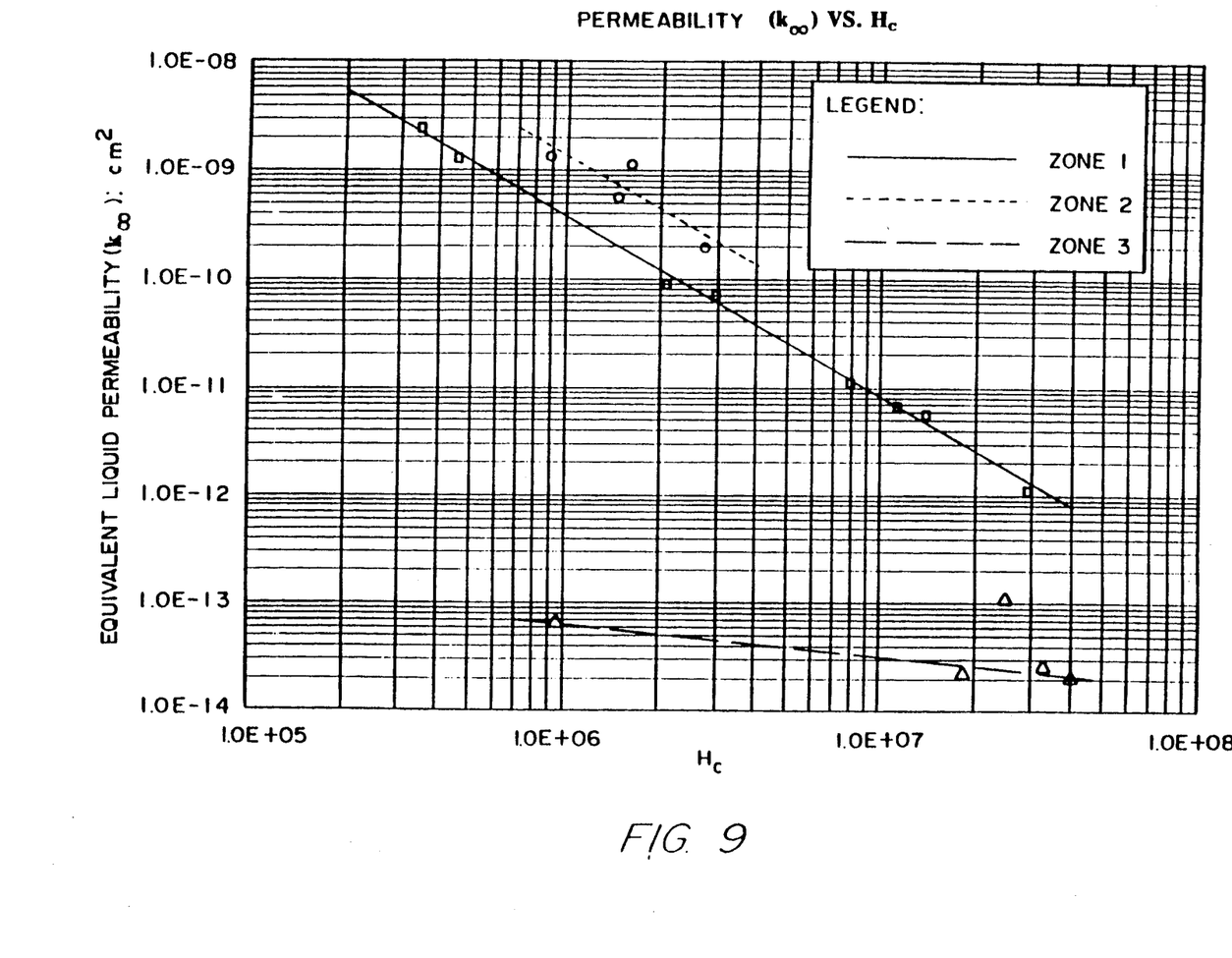
FIG. 9 is a graph showing an example of a plot of log ($k_\infty$) versus log ($H_c$)

Referring again to FIG. 2, the final step of the calibration process 14 is plotting $H_c$ versus $\phi$ and plotting $k \propto$ versus $H_c$ for each sample on which measurements were made. These graphs accurately identify distinct hydraulic units within several geologic units and establish a means for calculating permeability from the porosity measured in a given hydraulic unit. FIGS. 8 and 9 show the actual $H_c$ versus $\phi$ and k versus $H_c$ plots, respectively, determined by use of the foregoing method in connection with a sandstone formation (the Norphlet formation). As is evident from examination of FIGS. 8 and 9, the transformation process clearly identified three separate hydraulic units, each with a characteristic slope and limits. The method described herein identifies hydraulic units in either of sandstone or carbonate rocks.

Referring again to FIG. 1, the second step 13 of the method for logging for permeability is calibrating the logging tool. Typically, well logging tools are one of three different types. Resistivity (or induction) logging tools measure the ability of water coating reservoir rocks to conduct electric current. Salinity of the water tends to diminish resistance. Induction logs present an average measure of resistivity, and resolution vertically is generally restricted to rock units having a thickness greater than two feet.

Sonic logs measure the velocity of sound through rock grains and cements. Fluids trapped within the formation rocks tend to reduce the speed at which sound travels. Sonic logs present an average of formation measurements over several inches. Radioactive logs measure gamma and neutron radiation attenuation by dense rock and hydrogen compounds, respectively.

The precise details of the calibration step (13 in FIG. 1) will depend on the nature of the particular tool in use. Generally, however, calibration is accomplished by programming a digital computer by conventional techniques to transform porosity data derived from a wireline log to permeability data for which a transformation has been derived as described herein, by use of the relationships between log ($\phi$) and log ($H_c$) and between log (k) and log ($H_c$). This is accomplished by use of the general relationship $$k = \frac{\phi^3}{H_c(1-\phi)^2}, \quad (16)$$

where the hydraulic unit characterization factor, $H_c$, is unique for each hydraulic unit within the formation.

Once the hydraulic unit characterization factor, $H_c$, has been measured for a particular hydraulic unit, the calculation can be made on a real time basis to provide a log of permeability as a well is logged (step 14 in FIG. 1). Alternatively, permeability data can be generated by post-processing of porosity data previously logged from a plurality of wells. In either case, the foregoing method provides an accurate method for deriving reservoir permeability distributions from microscopic measurements on cores and macroscopic measurements on wireline logs.

WATER SATURATION DATA

The foregoing methods can be adapted to provide data other than permeability. For example, as explained below, one can apply the foregoing method to calibrate a tool to log a well for water saturation data.

Generally speaking, there are three methods currently used to determine water saturations in reservoirs. These include: (1) laboratory analysis of core samples taken with non-wetting drilling fluid; (2) electrical resistivity logging; and (3) calculating water distribution by capillary pressure measurements obtained from core samples. It is desirable to obtain data from all three methods to confirm the accuracy of one's measurements, using the laboratory measurements from methods (1) and (3), above, to calibrate the resistivity logs of method (2). Use of the effective zoning factor, $K_T$, as described in the preceding section, substantially improves the accuracy of water saturation as determined from capillary pressure measurements, thereby enhancing the accuracy of logs calibrated therefrom.

Capillary forces are controlled by pore size distributions, with small pore networks causing water to be drawn high above the water-oil contact point. The behavior of water saturation distributions above the free water level is expressed by the following relationships:

$$P_c = (\rho_w - \rho_o)gh = \frac{2\sigma \cos(\theta)}{r_p} \quad (17)$$

and $$h = \frac{2\sigma \cos(\theta)}{(\rho_w - \rho_o)g r_p}, \quad (18)$$

where $\rho_o$ is oil density (g/cc), $\rho_w$ is water density (g/cc), g is the universal gravitational constant, h is the water height above the water-oil contact point, $\bar{r}_p$ is the mean pore radius, $\sigma$ is the interfacial tension between water and oil, and $\theta$ is the contact angle of oil on a water wet surface.

Figure 10:
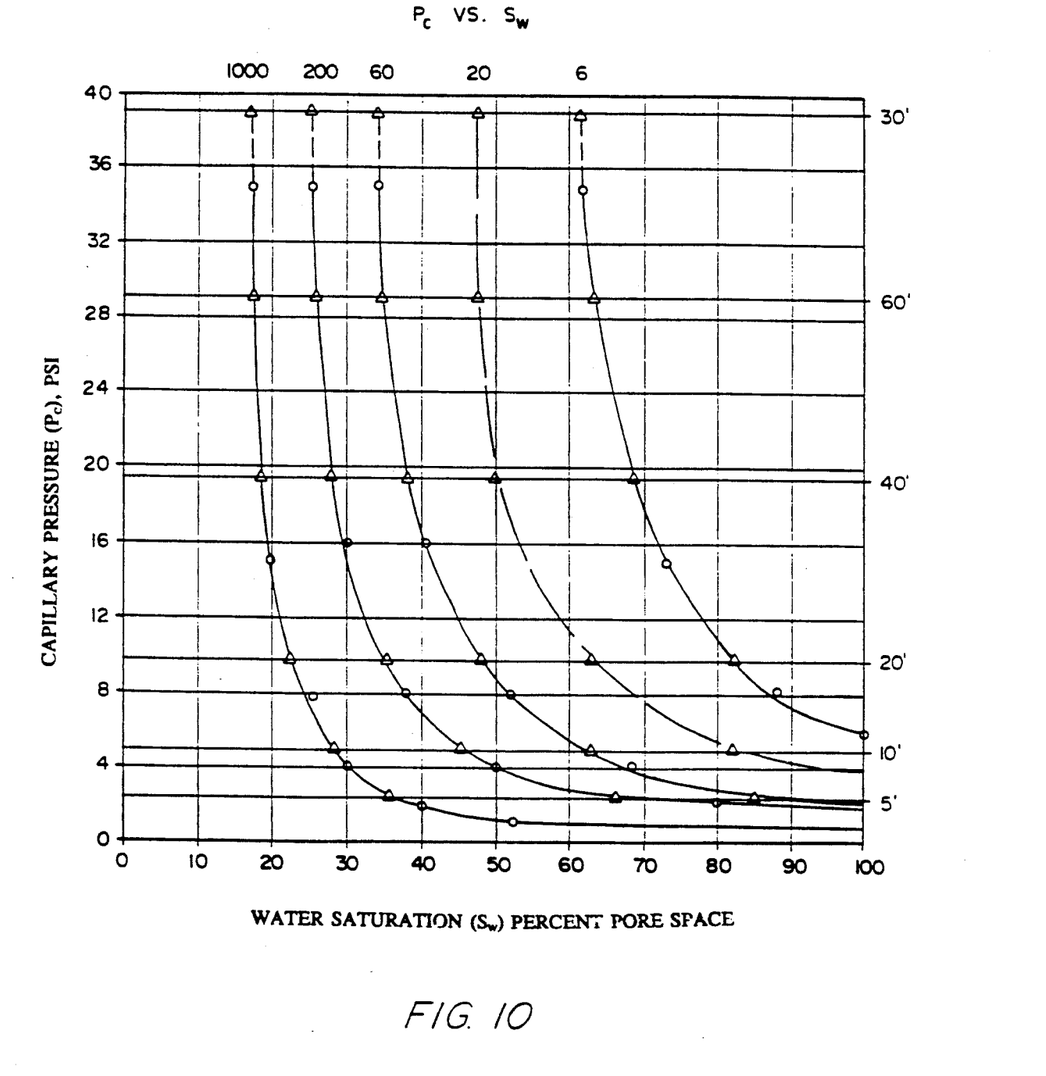
FIG. 10 is a graph of capillary pressure versus water saturation for discrete samples of formation material.

Traditionally, capillary pressure measurements are made on individual samples selected from each rock type. Water saturation is measured as a function of the pressure required to force water into the pores (capillary pressure). When water saturation, $S_w$, is plotted against capillary pressure, $P_c$, the result is a separate curve for each sample selected, as demonstrated by the graph shown in FIG. 10.

In order to normalize capillary pressure behavior, Leverett developed the so-called "J function".

$$J_L = \frac{P_c}{\sigma \cos(\theta)} \left(\frac{k}{\phi}\right)^{\frac{1}{2}}. \quad (19)$$

See M. C. Leverett, "Flow of Oil-Water Mixtures Through Unconsolidated Sands," 132 Transactions, AIME 149 (1939). The J function was intended to relate capillary behavior with water saturation distribution without data scatter. The amount of variability in Leverett's plot, however, has made the relationship less valuable than it could be. In accordance with the principles of the present invention, inclusion of the effective zoning factor, $K_T$, in the traditional J function yields an improved J function, $J_T$, as follows:

$$J_T = \frac{P_c(K_T)^{\frac{1}{2}}}{\sigma \cos(\theta)} \left(\frac{k}{\phi}\right)^{\frac{1}{2}}. \quad (20)$$

Figure 11:
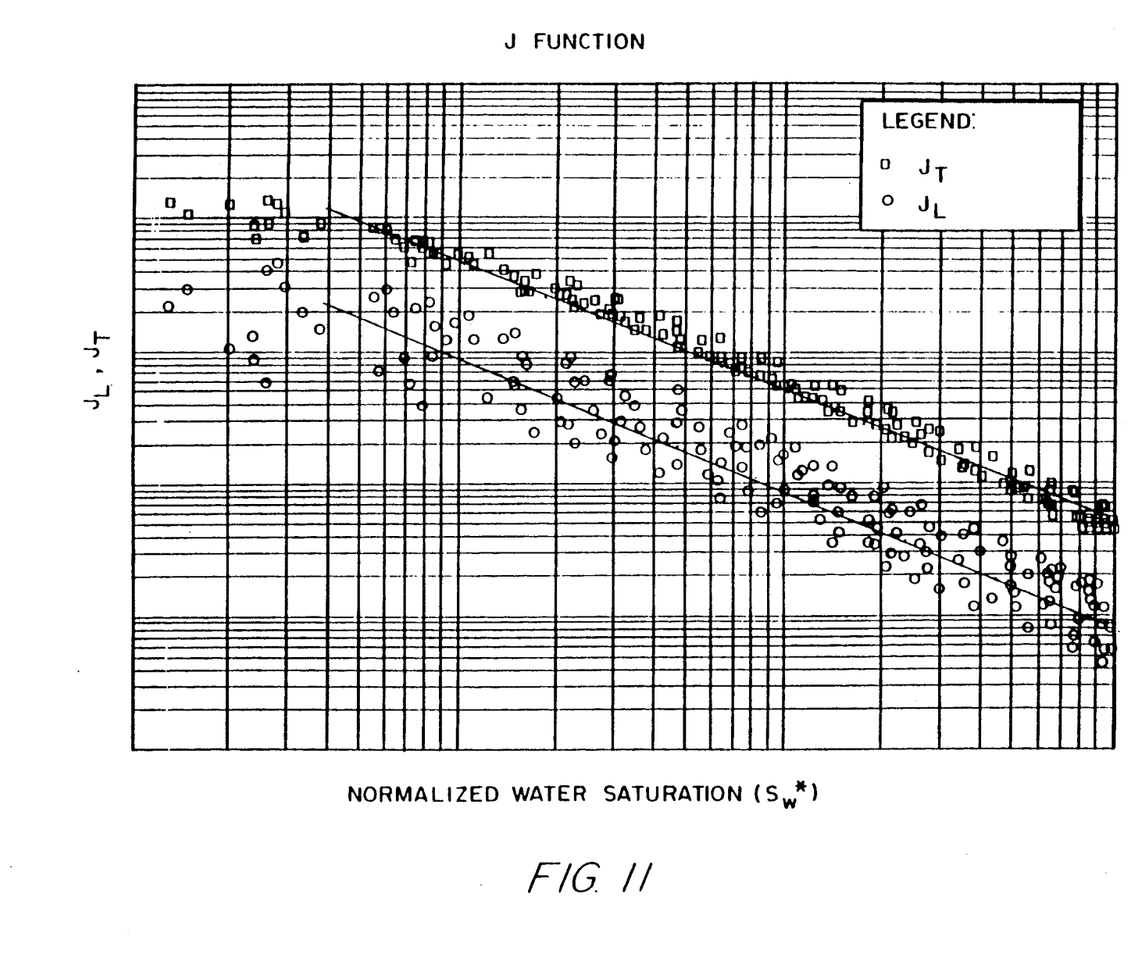
FIG. 11 is a log-log graph of J function and universal J function versus normalized water saturation for a particular formation.

The improved J function substantially enhances the ability to determine water saturation from capillary pressure data for a particular hydraulic unit. A graph showing the improved J function and the Leverett J function plotted against normalized water saturation, $S_w^*$, is shown in FIG. 11. Normalized water saturation, $S_w^*$, is determined as follows:

$$S_w^* = \frac{S_w - S_{wr}}{1 - S_{wr}}, \quad (21)$$

where $S_w$ and $S_{wr}$ are water saturation and residual water saturation, respectively. The plot of $J_T$ versus $S_w^*$ enables one to predict $S_w^*$ from any known capillary pressure for a particular hydraulic unit.

The improved predictability of water saturation can be used to enhance prediction of water saturation from a wireline log. Known in the art as the Archie equation, the following equation is used at present to predict water saturation from wireline resistivity logs:

$$S_w = \left(\frac{a}{\phi^m} \frac{R_w}{R_t}\right)^{\frac{1}{n}}, \quad (22)$$

where the variable a is a function of porosity, n is the saturation exponent, $R_w$ is the resistivity of water, $R_t$ is the total formation resistivity, and m is the cementation exponent. The values for a, m, and n in Equation (21) typically are determined both by field logging experience and by laboratory measurements of core plug samples. If the formation contains more than one hydraulic unit, and if the samples used for calibration are not truly representative of the formation being logged, the calibrations for a, m, and n will be inaccurate, as will the log of water saturation based thereon.

In accordance with the principles of the present invention, water saturation logging techniques can be improved by use of the methods disclosed herein. First, one can identify discrete hydraulic units by the methods disclosed previously. Then, one can plot $J_T$ versus $S_w^*$ for each hydraulic unit. This plot will enable one to identify samples that are representative of the hydraulic unit. Such samples can then be used to calibrate the logging tool to measure water saturation according to the following relationship:

$$S_w = \left(\frac{1}{K_c \phi^{m_t}} \frac{R_w}{R_t}\right)^{\frac{1}{n}}, \quad (23)$$

where $K_c$ is a cross-sectional shape factor, which is a function of porosity, $\phi$, as follows:

$$K_c = \phi^{(m_t - m)} \quad (24)$$

and $m_t$ is determined as follows:

$$m_t = 1 - \left(\frac{\log K_T}{\log \phi}\right). \quad (25)$$

Use of the foregoing method will enhance the accuracy of water saturation as determined from wireline logs.

While a preferred embodiment of the invention has been shown and described, modifications thereof can be made by one skilled in the art without departing from the spirit of the invention.

Appendix a: Archie variable (dimensionless)
$A_p$: pore cross-sectional area (cm$^2$)
$d_g$: grain diameter (cm)
$d_p$: pore diameter (cm)
g: universal gravitational constant (cm/s$^2$)
h: water height above the water-oil contact line (cm)
$H_c$: hydraulic unit characterization factor (cm$^{-2}$)
$H_{cg}$: hydraulic unit characterization factor based on the grain system (cm$^{-2}$)
$H_{cp}$: hydraulic unit characterization factor based on the pore system (cm$^{-2}$)
$J_L$: Levertt J-function (dimensionless)
$J_T$: Improved J-function (dimensionless)
$k_\infty$: klinkenberg permeability
k: permeability (cm$^{-2}$)
$K_c$: shape factor of a pore cross-sectional area (dimensionless)
$K_T$: effective zoning factor (dimensionless)
$L_p$: pore perimeter (cm)
m: cementation factor (dimensionless)
$m_t$: effective cementation factor (dimensionless)
n: saturation constant (dimensionless)
$P_c$: capillary pressure (dyne/cm$^2$)
$r_p$: mean pore radius (cm)
$r_{pt}$: mean pore throat radius (cm)
$R_t$: total formation resistivity (ohm-meter)
$R_w$: water resistivity (ohm-meter)
$S_w^*$: normalized water saturation (fraction)
$S_{gv}$: specific surface area per unit of grain volume (cm$^{-1}$)
$S_{pv}$: internal surface area of pore space per unit of pore volume (cm$^{-1}$)
$S_w$: water saturation (fraction)
$S_{wr}$: residual water saturation (fraction)
$\tau$: tortuosity (dimensionless)
$\sigma$: interfacial tension (dyne/cm)
$\theta$: contact angle (degrees)
$\phi$: porosity (fraction)
$\rho_o$: oil density (g/cc)
$\rho_w$: water density (g/cc)

What is claimed is:

1. A method for logging a formation for permeability, comprising:
   (a) defining geologic units of the formation based on analysis of core material from the formation;
   (b) obtaining plugs from the core material, wherein selection of the plugs is based on the geologic units definition;
   (c) determining a first set of hydraulic unit characterization factors based on core analysis of the plugs;
   (d) identifying hydraulic units distributed within the geologic units based on the first set of hydraulic unit characterization factors;
   (e) selecting a plurality of test samples of core material, wherein the selection is based on the hydraulic units distribution;
   (f) determining a second set of hydraulic unit characterization factors based on core analysis of the test samples;
   (g) determining a dynamic correlation between logging measurements and core analysis measurements of the formation based on the second set of hydraulic unit characterization factors;
   (h) calibrating a logging tool based on the correlation; and
   (i) logging a well in the formation with the calibrated logging tool to produce a permeability log of the formation.

2. The method of claim 1, wherein the first factors determination step (2) comprises:
   (c) (1) measuring permeability k and porosity $\phi$ of the plugs; and
   (c) (2) determining a first set of hydraulic unit characterization factors $H_c$ by calculating $H_c$ for the plugs, as follows:

$$H_c = \frac{\phi^3}{k(1-\phi)^2}$$

3. The method of claim 2, wherein the permeability and porosity measurements in step (c) (1) are made at overburden pressure conditions.

4. The method of claim 2, wherein the permeability and porosity measurements in step (c) (1) are made at a pressure of at least 800 pounds per square inch.

5. The method of claim 2, wherein the permeability measured in step (c) (1) is the equivalent liquid nonreactive permeability known as the Klinkenberg permeability, $k_\infty$.

6. The method of claim 1, wherein the hydraulic units identification step (d) comprises:
   (d) (1) plotting, on a logarithmic scale, the first set of hydraulic unit characterization factors versus the porosity measurements of the plugs;
   (d) (2) plotting, on a logarithmic scale the permeability measurements of the plugs versus the first set of hydraulic unit characterization factors; and
   (d) (3) identifying hydraulic units distributed within the geologic units, wherein each sloping line revealed by the plots corresponds to a different hydraulic unit within the geologic unit.

7. The method of claim 1, wherein the second factors determination step (f) comprises:
   (f) (1) determining a zoning factor $K_T$ for the test samples;
   (f) (2) determining a surface area parameter S for the test samples, wherein S is either a surface area of pore space per unit volume of pore space $S_{pv}$ or a surface area of grain per unit volume of grain $S_{gv}$; and
   (f) (3) determining a second set of hydraulic unit characterization factors $H_c$ for the formation, by calculating $H_c$ for the test samples, as follows:

$$H_c = K_T S^2$$

where S is either $S_{pv}$ or $S_{gv}$.

8. The method of claim 7, wherein the zoning factor $K_T$ in step (f) (1) is calculated for the test samples, as follows:

$$K_T = \pi K_{sp}$$

where $\pi$ is tortuosity and $K_{sp}$ is a pore shape factor for the test sample.

9. The method of claim 8, wherein the tortuosity, $\pi$, is calculated for the test samples, as follows:

$$\tau = \phi^{(1-m)}$$

where m is the cementation factor.

10. The method of claim 7, wherein the surface area parameter determination step (f) (2), comprises determining a surface area parameter S for each test sample by measuring either a surface area of pore space per unit volume of pore space $S_{pv}$ or a surface area of grain per unit volume of grain $S_{gv}$ for each test sample.

11. The method of claim 7, wherein the surface area parameter determination step (f) (2) comprises:
   (f) (2) (i) measuring either a surface area of pore space per unit volume of pore space $S_{pv}$ or a surface area of grain per unit volume of grain $S_{gv}$ of one test sample;
   (f) (2) (ii) measuring either pore diameters $d_p$ or grain diameters $d_g$ of the test samples;
   (f) (2) (iii) determining either a pore shape factor $K_{sp}$ or a grain shape factor $K_{sg}$ for the formation as follows:

$$K_{sp} = d_p S_{pv}$$

or $$K_{sg} = d_g S_{gv}$$

where $d_p$ is the pore diameter and $d_g$ is the grain diameter of the test sample used in step (f) (2) (i) to measure either $S_{pv}$ or $S_{gv}$; and (f) (2) (iv) calculating a surface area parameter S for the test samples, as follows:

$$S = S_{pv} = \frac{K_{sp}}{d_p} \text{ or } S = S_{gv} = \frac{K_{sg}}{d_g}.$$

12. The method of claim 7, wherein the second factors determination step (f) further comprises:
   (f) (4) identifying hydraulic units distributed within the formation based on the second set of hydraulic unit characterization factors;
   (f) (5) determining if the hydraulic units distribution requires adjustment based on a comparison of the hydraulic units identified in steps (d) and (f) (4); and
   (f) (6) repeating the test sample determination step (e) and the second factors determination steps, (f)

(1-3), based on an adjusted hydraulic units distribution.

13. The method of claim 7, wherein the dynamic correlation determination step, (g), comprises:
(g) (1) plotting, on a logarithmic scale, the second set of hydraulic unit characterization factors versus formation depth; and
(g) (2) determining a dynamic correlation between log measurements and core analysis measurements based on the relationships disclosed in the plot.

* * * * *